United States Patent [19]

Tomioka et al.

[11] 4,132,846

[45] Jan. 2, 1979

[54] 1-N-(α-HYDROXY-β-AMINOPROPIONYL) XK-62-2 AND METHOD OF PRODUCTION THEREOF

[75] Inventors: Shinji Tomioka, Machida; Yasuki Mori, Kawasaki, both of Japan; Kunikatsu Shirahata, Columbus, Ohio

[73] Assignee: Abbott Laboratories, North Chicago, Ill.

[21] Appl. No.: 775,463

[22] Filed: Mar. 8, 1977

Related U.S. Application Data

[63] Continuation of Ser. No. 556,223, Mar. 7, 1975, abandoned.

[30] Foreign Application Priority Data

Mar. 7, 1974 [JP] Japan .................................. 49-25753

[51] Int. Cl.$^2$ ............................................. C07H 15/22
[52] U.S. Cl. ..................................... 536/17; 424/180; 536/10

[58] Field of Search ......................................... 536/17

[56] References Cited

U.S. PATENT DOCUMENTS

| | | | |
|---|---|---|---|
| 3,780,018 | 12/1973 | Konishi et al. | 536/17 |
| 3,796,699 | 3/1974 | Naito et al. | 536/17 |
| 4,028,188 | 6/1977 | Daum et al. | 536/17 |
| 4,029,882 | 6/1977 | Wright | 536/17 |
| 4,055,715 | 10/1977 | Tomioka et al. | 536/17 |

*Primary Examiner*—Johnnie R. Brown
*Attorney, Agent, or Firm*—Fitzpatrick, Cella, Harper & Scinto

[57] ABSTRACT

1-N-(α-Hydroxy-β-aminopropionyl) XK-62-2 is produced by chemically modifying the antibiotic XK-62-2 to introduce an β-hydroxy-β-aminopropionyl group to the amino group bonded to the carbon atom at the 1-position. The derivative is useful as an antibacterial agent.

1 Claim, 7 Drawing Figures

1-N-(α-HYDROXY-β-AMINOPROPIONYL) XK-62-2 AND METHOD OF PRODUCTION THEREOF

This a continuation of application Ser. No. 556,223, filed Mar. 7, 1975 now abandoned.

RELATED APPLICATIONS

The present application is directed to a derivative of the antibiotic XK-62-2. The latter mentioned and the fermentative production thereof is described and claimed in U.S. Patent Application Ser. No. 364,058, filed May 25, 1973. Other patent applications relating to semi-synthetic derivative of XK-62-2 are Ser. No. 531,769 and 531,768 filed Dec. 11, 1974 and Ser. No. 542,950 filed Jan. 22, 1975.

BACKGROUND OF THE INVENTION

The present invention relates to a derivative of the antibiotic XK-62-2 and more specifically to the derivative identified as 1-N-(α-hydroxy-β-aminopropionyl) XK-62-2 and the production thereof. In the present invention the derivative may be in D-, L- or DL-form.

Briefly stated, as disclosed in the aforementioned U.S. Patent Application Ser. No. 364,058, antibiotic XK-62-2 is produced by culturing actinomycetes suh as *Micromonospora sagamiensis*, *Micromonospora echinospora* and *Micromonospora purpurea* by methods usually employed in the culturing of actinomycetes. More specifically, strains of the above-mentioned microorganisms such as *Micromonospora sagamiensis* ATCC 21826, ATCC 21827, ATCC 21803 and ATCC 21949 are inoculated into a liquid medium containing a carbon source which the microorganism can utilize such as sugars, hydrocarbons, alcohols, organic acids, etc.; inorganic or organic nitrogen sources and inorganic salts and growth promoting factors and are cultured at 25°–40° C. for 2 to 12 days until substantial antibacterial activity is detected in the culture liquor. Isolation and purification of XK-62-2 is carried out by a combination of adsorption and desorption from ion exchange resins and active carbon and column chromatography using cellulose, Sephadex, alumina and silica gel. In this manner, XK-62-2 can be obtained in the form of a salt or as a free base.

XK-62-2 is a basic substance and is obtained as a white powder. XK-62-2 has a molecular formula of $C_{20}H_{41}N_5O_7$, and a molecular weight of 463. The substance is freely soluble in water and methanol, slightly soluble in ethanol and acetone and insoluble in chloroform, benzene, ethyl acetate and n-hexane.

SUMMARY OF THE INVENTION

In accordance with the present invention a new antibacterial compound is produced by chemically modifying the antibiotic XK-62-2 having the following structural formula:

The derivative of XK-62-2 of the present invention exhibits a strong antibacterial activity against a variety of Gram-positive and Gram-negative bacteria and particularly has a remarkably strong antibacterial activity against those bacteria that are resistant to the known aminoglycoside antibiotics including XK-62-2. Accordingly, the antibiotic of the invention is useful to clean and disinfect laboratory glassware and surgical instruments, and may also be used in combination with various soaps for sanitation purposes and in cleaning and sanitizing hospital rooms and areas used for the preparation of food. Further, the derivative is expected to be effective for the treatment of various infections such as urinary tract infections and respiratory infections induced by various phlogogenous bacteria, for example, *Staphylococcus aureus*, *Sarcina lutea*, *Escherichia coli*, *Pseudomonas aeruginosa* and *Proteus*.

More specifically, the new derivative of XK-62-2 or its pharmaceutically acceptable, non-toxic acid addition salts is prepared by introducing an α-hydroxy-β-aminopropionyl group to the amino group bonded to the carbon atom at the 1-position of XK-62-2.

Thus, in accordance with the present invention, 1-N-α-hydroxy-β-aminopropionyl) XK-62-2 having the formula:

is prepared by acylating XK-62-2 with an acylating agent capable of introducing an α-hydroxy-β-substituted aminopropionyl group to an amino group, to prepare an intermediate compound and thereafter eliminating the substituted protecting groups in a known manner. If desired, 1-N-(α-hydroxy-β-aminopropionyl) XK-62-2 may be thereafter converted to non-toxic acid addition salts by conventional methods.

In a more preferred method, an enhanced yield of the compound of the invention can be obtained by protecting the amino groups bonded to the carbon atoms at the 2'- and/or 6'-positions of XK-62-2 with suitable protecting groups prior to the acylation reaction for introducing an α-hydroxy-β-substituted aminopropionyl group.

DESCRIPTION OF THE INVENTION

I. Acylation of XK-62-2

In accordance with the present invention the free base of the compound, XK-62-2, is reacted with an acylating agent, i.e. a compound capable of introducing an α-hydroxy-β-substituted aminopropionyl group wherein at least one of the hydrogen atoms of the β-amino group is substituted by a protecting group in a suitable solvent to prepare an intermediate compound having one of the hydrogen atoms of the amino group bonded to the carbon atom at the 1-position of XK-62-2 substituted by said acyl group.

As the acylating agent, α-hydroxy-β-substituted aminopropionic acid and its derivatives having an acylating ability may be used. The acylating agent may be in D-, L- or DL-form.

The reaction is carried out in one or more solvent selected, depending upon the acylating agent, from the group consisting of tetrahydrofuran, dimethyl formamide, dimethylacetamide, lower alcohols, dioxane, ethylene glycol dimethylether, pyridine and water. If necessary, a dehydrating and/or condensing agent such as dicyclohexylcarbodiimide is added thereto. The reaction temperature is −50° to 50° C., preferably, −20° to 20° C.

Usually, 0.4–2.5 moles, preferably, 0.7–1.5 moles of the acylating agent is used per one mole of XK-62-2. When an increased amount, for example, 5 moles of the acylating agent is used or where the reaction is carried out at an elevated temperature of, for example, 100° C., reaction may proceed but the selectivity of the position to which the acyl group is introduced is greatly reduced or, otherwise, the acylating agent decomposes. Consequently, the production yield of the intermediate compound in the reaction mixture is decreased.

For the protecting group of the acylating agent, any readily eliminable protecting group usually used in peptide syntheses may be used. Such protecting group and the corresponding protecting reagent which can introduce the protecting group are described in M. Bodanszky et al: Peptide Synthesis, pages 21–41 (1966) (John Wiley & Sons, Inc., U.S.A.); and A. Kapoor: Journal of Pharmaceutical Sciences, Vol. 59, pages 1–27 (1970).

Examples of the preferred protecting groups and the corresponding reagents are shown in Table 1 below.

Table 1

Table 1-continued

In the protecting groups and protecting reagents set forth in Table I above, $R_1$ and $R_2$ may be the same or different and are H, OH, $NO_2$, Cl, Br, I, alkyl groups having 1 to 5 carbon atoms or alkoxy groups having 1 to 5 carbon atoms, $R_3$ is H, F, Cl, Br, I or an alkyl group having 1 to 5 carbon atoms and X is Cl, Br or I.

As the above-described derivatives of α-hydroxy-β-substituted aminopropionic acid, which have the ability to acylate and are used as the acylating agent, acid halides, acid azide, mixed acid anhydrides and reactive esters may be mentioned. Such derivatives are usually used in peptide syntheses. Examples of these derivatives are described in M. Bodanszky et al: Synthesis, page 453 (1972); and in M. Bodanszky et al: Peptide Synthesis, pages 75–135 (1966) (John Wiley & Sons, Inc., U.S.A.).

As preferred derivatives, those having a structure with the hydroxy group of the carboxy group of α-hydroxy-β-substituted aminopropionic acid substituted by one of the following groups are appropriate:

wherein $R_4$ is an alkyl group having 1 to 7 carbon atoms or a phenyl group. Particularly preferred derivatives are those having a structure with the OH group substituted by Thus, various acylating agents are proposed. Among them, N-hydroxy succinimide ester of α-hydroxy-β-carbobenzoxyaminopropionic acid of the formula:

is recommended as the most preferred.

This acylating agent is prepared by reacting α-hydroxy-β-carbobenzoxyaminopropionic acid with N-hydroxysuccinimide in the presence of a dehydrating and condensing agent, for example, dicyclohexylcarbodiimide. The acylating agent prepared in this manner can, of course, be isolated from the reaction mixture and then reacted with XK-62-2 or the reaction mixture may be directly reacted with XK-62-2 without isolating the acylating agent.

It is to be understood that derivatives of α-hydroxy-β-substituted aminopropionic acid wherein the hydroxy group of the carboxy group is substituted by other groups than that disclosed above can be prepared in a known manner and are acceptable for the reaction of the invention.

The thus prepared intermediate compound may be isolated and purified from the reaction mixture and used as the starting material for the subsequent reaction. However, it is preferred that after the completion of reaction, the reaction mixture be used as the starting material for the subsequent reaction without purification. The latter method is advantageous in simplifying the steps and enhancing the yield of recovery.

If necessary, the intermediate compound may be readily isolated and purified by conventional methods, for example, column chromatography using adsorbents such as ion exchange resins, silica gel, alumina and cellulose or thin layer chromatography using silica gel, alumina and cellulose.

II. Elimination of the protecting group

The protecting group of the amino group contained in the intermediate compound prepared in the above step I is thereafter eliminated to prepare 1-N-(α-hydroxy-β-aminopropionyl) XK-62-2.

Elimination of the protecting group may be carried out by conventional methods. For example, where the protecting groups form a phthaloyl group, elimination is accomplished with hydrazine, where the protecting group is a carbomethoxy group or carboethoxy group, elimination is accomplished with barium hydroxide; where the protecting group is a tertiary butoxycarbonyl group, elimination is accomplished with formic acid or trifluoroacetic acid; where the protecting group is a trityl group, elimination is accomplished with acetic acid or trifluoroacetic acid; where the protecting group is an orthonitrophenylsulphenyl group, elimination is accomplished with acetic acid or hydrochloric acid; and where the protecting group is a chloroacetyl group, elimination is accomplished with 3-nitropyridine-2-thione [reported by K. Undheim et al: Journal of the Chemical Society, Perkin Transactions, Part I, page 829 (1973)].

In a preferred embodiment, the protecting group of the intermediate compound is a benzyloxycarbonyl group and elimination is carried out by hydrogenolysis in the presence of a metal catalyst selected from palladium, platinum, rhodium and Raney nickel, preferably, palladium catalyst on a carrier of active carbon in at least one solvent selected from the group consisting of water, tetrahydrofuran, dimethylacetamide, dimethylformamide, lower alcohols, dioxane, ethylene glycol dimethyl ether, and/or pyridine, preferably, a mixture of water and methanol (1:1); in the presence of a small amount of hydrochloric acid, hydrobromic acid, hydriodic acid or acetic acid, preferably, acetic acid, and at room temperature and at atmospheric pressure.

The thus prepared 1-N-(α-hydroxy-β-aminopropionyl) XK-62-2 is isolated and purified from the reaction mixture in a known manner. For example, the compound is isolated and purified by column chromatography using an adsorbent such as ion exchange resins, silica gel, alumina, cellulose, Sephadex, etc., or thin layer chromatography using silica gel, alumina, cellulose, etc.

If desired, 1-N-(α-hydroxy-β-aminopropionyl) XK-62-2 prepared in accordance with the above may be converted to pharmaceutically acceptable, non-toxic acid addition salts (mono-, di-, tri-, tetra or penta salts) according to conventional methods such as by interacting one molecule of the compound with one to five moles of a non-toxic pharmaceutically acceptable acid. In the present invention, nontoxic acids include inorganic acids such as hydrochloric acid, hydrobromic acid, hydriodic acid, sulfuric acid, phosphoric acid, carbonic acid, etc. and organic acids such as acetic acid, fumaric acid, malic acid, citric acid, mandelic acid, tartaric acid, ascorbic acid, etc.

Although the foregoing method accomplishes the object of the invention, it has been found that by blocking specific amino groups of XK-62-2, the yield of the compound of the invention can be enhanced.

As mentioned above, the compound of the invention is prepared by introducing α-hydroxy-β-aminopropionyl group to the amino group bonded to the carbon atom at the 1-position of XK-62-2. It has been found that among the amino groups possessed by XK-62-2, the amino group bonded to the carbon atom at the 2'-position is more reactive than that bonded to the carbon atom at the 1-position. Accordingly, it is preferable to protect the amino group bonded to the carbon atom at the 2'-position prior to acylation reaction to introduce α-hydroxy-β-aminopropionyl group. It has also be found that although the amino group bonded to the carbon atom at the 3-position is less reactive than that bonded to the carbon atom at the 1-position, it becomes much less reactive when the hydrogen atom attached to the nitrogen atom of the amino group bonded to the carbon atom at the 6'-position is substituted by a protecting group. It has further been found that the amino group bonded to the carbon atom at the 3''-position is much less reactive than that bonded to the carbon atom at the 1-position. Accordingly, it is desirable that both the amino groups bonded to the carbon atoms at the 2'- and 6'-positions be protected prior to the acylation reaction.

Practically, when protection of the amino group bonded to the carbon atom at the 2'-position is attempted, a compound having the amino group bonded to the carbon atom at the 2'-position protected, a compound having the amino groups bonded to the carbon atoms at the 2'- and 6'-positions protected and a compound having the amino group bonded to the carbon atom at the 6'-position protected are produced as a mixture.

A. Protection of the amino groups bonded to the carbon atoms at the 2'- and/or 6'positions XK-62-2 is reacted with an amino-protecting reagent in a suitable solvent to prepare at least one of: a compound having a structure with the hydrogen atom attached to the nitrogen atom of the methylamino group bonded to the carbon atom at the 6'-position of XK-62-2 substituted (intermediate compound IIA); a compound having a structure with at least one of the hydrogen atoms of the amino group bonded to the carbon atom at the 2'-position of XK-62-2 substituted (intermediate compound IIB); and a compound having a structure with the hydrogen atom attached to the nitrogen atom of the methylamino group bonded to the carbon atom at the 6'-position and at least one of the hydrogen atoms of the amino group bonded to the carbon atom at the 2'-position of XK-62-2 substituted (intermediate compound IIC). Usually, these intermediate compounds are obtained as a mixture.

The reaction of XK-62-2 with the amino-protecting reagent is carried out under the conditions usually employed in conventional methods of protecting amino groups such as described above. Generally, 0.5 mole to 4.5 moles of the protecting reagent is used per one mole of XK-62-2. The reaction is carried out at −50° C. to 50° C.

In this case, it is not desirable to use an increased amount of the protecting reagent or to carry out the reaction at an elevated temperature, because, under such conditions, the protecting group is also introduced to the amino group bonded to the carbon atom at the 1-position. In order to selectively protect only those amino groups bonded to the carbon atoms at the 2'- and/or 6'-positions, it is recommended to use 0.7 mole to 2.6 moles of the protecting agent per one mole of XK-62-2 and to carry out the reaction at a temperature of −20° to 20° C.

The solvent for the reaction may be at least one selected from the group consisting of tetrahydrofuran, dimethylacetamide, dimethylformamide, lower alcohols, dioxane, ethylene glycol dimethyl ether, pyridine and/or water.

For the amino-protecting reagent, any of the protecting reagents capable of introducing readily eliminable protecting groups that are usually employed in peptide syntheses may be used. Preferred protecting reagents are compounds set forth in Table 1 above.

The intermediate compounds IIA, IIB and IIC of XK-62-2 can be used for the subsequent reaction as is, without isolation and purification. However, if desired, the intermediate compounds can be isolated and purified by conventional methods.

B. Acylation of the amino group bonded to the carbon atom at the 1-position

At least one of the intermediate compounds IIA, IIB and IIC prepared in the above step A is reacted with an acylating agent, i.e. α-hydroxy-β-substituted aminopropionic acid or derivatives thereof having the ability to acylate in a suitable solvent to prepare at least one of an intermediate compound IIIA having a structure with one of the hydrogen atoms of the amino group bonded to the carbon atom at the 1-position of the intermediate compound IIA substituted by an α-hydroxy-β-sutstituted aminopropionyl group; an intermediate compound IIIB having a structure with one of the hydrogen atoms of the amino group bonded to the carbon atom at the 1-position of the intermediate compound IIB substituted by a α-hydroxy-β-substituted aminopropionyl group; and an intermediate compound IIIC having a structure with one of the hydrogen atoms of the amino group bonded to the carbon atom at the 1-position of the intermediate compound IIC substituted by α-hydroxy-β-substituted aminopropionyl group.

The acylation step and that of isolation of the intermediate compounds IIIA, IIIB and IIIC can be carried out in the same manner as described in the acylation step I of XK-62-2 above, except that 0.5–1.5 moles, preferably, 0.7–1.2 moles of the acylating agent is used per one mole of the compound IIA, IIB and IIC. When an increased amount, for example, 3 moles of the acylating agent is used or where the reaction is carried out at an elevated temperature of, for example 100° C., the reaction may proceed but the selectivity of the position to which an α-hydroxy-β-substituted aminopropionyl group is introduced is reduced or, otherwise, the acylating agent decomposes. Consequently, the production yields of the intermediate compounds IIIA, IIIB and IIIC are decreased.

C. Elimination of the protecting group

Elimination of the protecting groups from the thus prepared compounds IIIA, IIIB and IIIC to prepare 1-N-(α-hydroxy-β-aminopropionyl) XK-62-2 is carried out in the same manner as described above. Moreover, conversion of the resulting compounds to non-toxic acid addition salts is carried out by methods well known in the art.

The products obtained by elimination of the protecting group from the intermediate compounds exhibit the same characteristics in NMR spectrum, infrared absorption spectrum, melting point, specific rotation, elementary analysis and MIC against various bacteria. Based on these data, the products are identified as 1-N-(α-hydroxy-β-aminopropionyl) XK-62-2.

1-N-(α-hydroxy-β-aminopropionyl) XK-62-2 of the present invention has an excellent antibacterial activity. It is particularly notable that the compound has a strong antibacterial activity against strains of *Escherichia coli* having R factors which show resistance to known aminoglycoside antibiotics.

Table 2 illustrates the antibacterial spectrum of kanamycin A, gentamicin $C_{1a}$, XK-62-2 and D-, L- and DL-forms of 1-N-(α-hydroxy-β-aminopropionyl) XK-62-2 against various Gram-negative and Gram-positive bacteria determined by agar dilution method at pH 8.0.

From a comparison of the minimum inhibitory concentration shown in Table 2, it is apparent that the present compound has a strong antibacterial activity. Characteristically, the compound shows a strong antibacterial activity particularly against *Escherichia coli* KY 8327 and 8348.

Table 2

| | Anti-bacterial Spectrum (minimum Inhibitory Concentration, mcg/ml) | | | | | |
|---|---|---|---|---|---|---|
| | | | | 1-M-($\alpha$-Hydroxy-$\beta$-amino-propionyl)—XK-62-2 | | |
| Strains | Kanamycin A | Gentamicin $C_{1a}$ | XK-62-2 | D-form | L-form | DL-form |
| *Pseudomonas aeruginosa* BMH 1 | 5.2 | 0.13 | 0.52 | 2.08 | 1.04 | 1.04 |
| *Staphylococcus aureus* ATC 6538P | 0.021 | 0.004 | 0.008 | 0.004 | 0.004 | 0.065 |
| *Bacillus subtilis* No. 10707 | 0.021 | 0.004 | 0.004 | 0.004 | 0.004 | 0.008 |
| *Proteus vulgaris* ATCC 6897 | 0.16 | 0.033 | 0.033 | 0.033 | 0.033 | 0.033 |
| *Shigella sonnei* ATCC 9290 | 0.16 | 0.033 | 0.033 | 0.008 | 0.008 | 0.016 |
| *Salmonella typhosa* ATCC 9992 | 0.08 | 0.016 | 0.008 | 0.004 | 0.004 | 0.004 |
| *Klebsiella pneumoniae* ATCC 10031 | 0.042 | 0.016 | 0.004 | 0.004 | 0.004 | 0.033 |
| *Escherichia coli* ATC 26 | 0.16 | 0.033 | 0.016 | 0.004 | 0.004 | 0.008 |
| *Escherichia coli* KY 8327 | 1.04 | 2.08 | 1.04 | 0.004 | 0.004 | 0.004 |
| *Escherichia coli* KY 8348 | 0.041 | 1.04 | 1.04 | 0.004 | 0.004 | 0.004 |

In the above table, *Escherichia coli* KY 8327 and KY 8348 respectively produce gentamicin adenyltransferase and gentamicin acetyltransferase Type I intracellularly. The former bacterium inactivates kanamycins and gentamicins by adenylation, and the latter inactivates gentamicins by acetylation.

Further, the antibacterial spectra of 1-N-($\alpha$-hydroxy-$\beta$-aminopropionyl) XK-62-2 (in D-, L- and DL-forms) in comparison with kanamycin A, gentamicin C complex ($C_1$, $C_{1a}$ and $C_2$) and XK-62-2 measured by agar dilution method at pH 7.2 are shown in Table 3 below.

transferase Type I and Type II intracellularly, thereby inactivating gentamicin antibiotics and XK-62-2.

Practice of certain specific embodiments of the present invention is illustrated by the following representative examples. In the examples, DL-form of the acylating agent is used.

EXAMPE 1

Production of 6'-N-carbobenzoxy XK-62-2, 2'-N-carbobenzoxy XK-62-2 and 2'-N, 6'-N-dicarbobenzoxy XK-62-2

In this example, 4.00 g (8.65 mmoles) of XK-62-2 is

Table 3

| | Anti-bacterial Spectrum (Minimum Inhibitory Concentration, mcg/ml) | | | | | |
|---|---|---|---|---|---|---|
| | | Gentamicin C complex | | 1-N-($\alpha$-Hydroxy-$\beta$-amino-propionyl)-XK-62-2 | | |
| Strains | Kanamycin A | ($C_1$, $C_{1a}$ and $C_2$) | XK-62-2 | D-form | L-form | DL-form |
| *Staphylococcus aureus* 209 P | 0.2 | <0.05 | 0.1 | 0.05 | 0.05 | 0.1 |
| *Staphylococus aureus* Smith | 0.2 | <0.05 | <0.05 | — | — | 0.05 |
| *Bacillus subtilis* ATCC 6633 | 0.2 | <0.05 | <0.05 | 0.05 | 0.05 | 0.1 |
| *Sarcina lutea* ATCC 9341 | 6.25 | 0.2 | 0.4 | — | — | 0.4 |
| *Escherichia coli* T-2 | 1.56 | 0.4 | 0.4 | 0.2 | — | 0.4 |
| *Escherichia coli* T-5 | 1.56 | 0.4 | 0.4 | — | — | 0.4 |
| *Escherichia coli* KY 8327[1] | 50 | 12.5 | 12.5 | 0.2 | 0.2 | 0.4 |
| *Escherichia coli* KY 8321[2] | 100 | 6.25 | 3.12 | 0.2 | 0.4 | 0.2 |
| *Escherichia coli* KY 8348[3] | 0.78 | 3.12 | 12.5 | 0.2 | 0.2 | 0.2 |
| *Escherichia coli* KY 8349[4] | >100 | 0.2 | 0.4 | 0.2 | 0.2 | 0.2 |
| *Pseudomonas aeruginosa* BMH 1 | 12.5 | 0.4 | 0.78 | 1.56 | 1.56 | 1.56 |
| *Pseudomonas aeruginosa* KY 8510[5] | 100 | 3.12 | 1.56 | 3.12 | 3.12 | 3.12 |
| *Pseudomonas aeruginosa* KY 8511[6] | 100 | 50 | 100 | 3.12 | 3.12 | 3.12 |
| *Pseudomonas aeruginosa* KY 8512[7] | 12.5 | 0.4 | 0.78 | 1.56 | 0.78 | 0.78 |
| *Pseudomonas aeruginosa* KY 8516[8] | >100 | 3.12 | 3.12 | — | — | 3.12 |
| *Providencia sp.* 164[9] | >100 | 50 | 100 | 6.25 | 6.25 | 12.5 |
| *Klebsiella pneumoniae* No. 8045 | 0.4 | 0.2 | 0.1 | 0.2 | 0.2 | 0.2 |
| *Proteus mirabilis* 1287 | 6.25 | 1.56 | 0.78 | 3.12 | 3.12 | 3.12 |
| *Proteus vulgaris* 6897 | 3.12 | 0.78 | 0.78 | 0.78 | 1.56 | 3.12 |
| *Proteus rettgeri* KY 4288 | 0.78 | 0.78 | 0.4 | — | — | 0.78 |
| *Proteus morganii* KY 4298 | 1.56 | 0.78 | 0.4 | — | — | 0.78 |

[1] produces gentamicin adenyltransferase
[2] produces gentamicin adenyltransferase and neomycin-kanamycin phosphotransferase Type II
[3] produces gentamicin acetyltransferase Type I
[4] produces neomycin-kanamycin phosphototransferase Type I
[5] produces kanamycin acetyltransferase
[6] produces gentamicin acetyltransferase Type I and neomycin-kanamycin phosphotransferase Type I
[7] produces neomycin-kanamycin phosphotransferase Type I and Type II and streptomycin phosphotransferase
[8] probably produces kanamycin acetyltransferase
[9] produces gentamicin acetyltransferase Type II
The foregoing enzymes are produced intracellularly and, with the enzymes, the bacteria inactivate antibiotics.

From the above Table 3, it is apparent that 1-N-($\alpha$-hydroxy-$\beta$-aminopropionyl) XK-62-2 of the present invention has a very strong antibacterial activity against various bacteria having a resistance to at least one of gentamicin antibiotics and XK-62-2, which produce gentamicin adenyltransferase and/or gentamicin acetyldissolved in 92 ml of aqueous 50% dimethylformamide. To the solution is added dropwise a solution of 3.23 g (12.9 mmoles) of N-benzyloxycarbonyloxysuccinimide in 70 ml of dimethylformamide with stirring while maintaining the temperature at 0° C. to 5° C. The addition is complete in 3 hours. The mixture is allowed to stand at 0° C. to 5° C. overnight. By silica gel thin layer chromatography (developer : isopropanol : concentrated aqueous ammonia : chloroform = 4:1:1, color reagent : ninhydrin), the presence of unreacted XK-62-2 in addition to 6'-N-carbobenzoxy XK-62-2 (Rf : 0.71), 2'-N-carbobenzoxy XK-62-2 (Rf : 0.62) and 2'-N, 6'-N-dicarbobenzoxy XK-62-2 (Rf : 0.88) is confirmed.

EXAMPLE 2

Production of 2'-N, 6'-N-dicarbobenzoxy XK-62-2

In this example, the reaction mixture obtained in Example 1 above is concentrated under reduced pressure. To the resulting residue are added 70 ml of water and 50 ml of ethyl acetate and the resulting mixture is stirred vigorously. The mixture is then allowed to stand to separate into two layers (water layer and ethylacetate layer). The water layer is extracted twice with 30 ml of ethylacetate. The ethylacetate layer and the ethylacetate extracts are combined, dried with anhydrous sodium sulfate and evaporated to dryness. As a result 2.24 g of 2'-N, 6'-N-dicarbobenzoxy XK-62-2 is obtained as a light yellow, amorphous solid. Yield : 35.1%. The thus obtained sample may be directly used as a starting material for the subsequent reaction. However, if desired, the product may be further purified by silica gel column chromatography (developer : isopropanol : concentrated aqueous ammonia : chloroform = 4 : 1 : 1).

Figure 1:
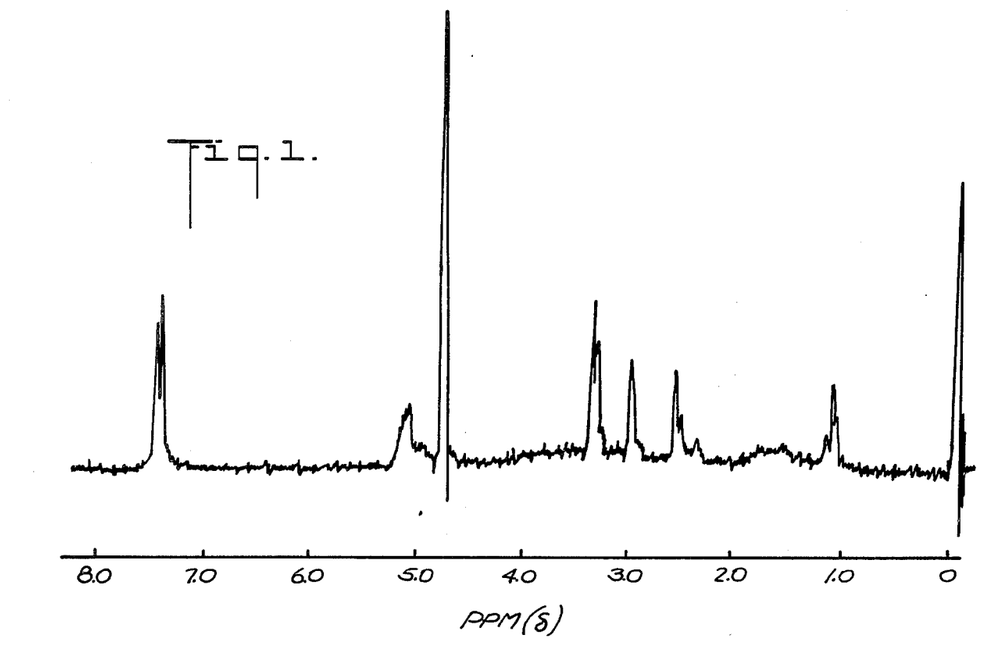
Figure 4:
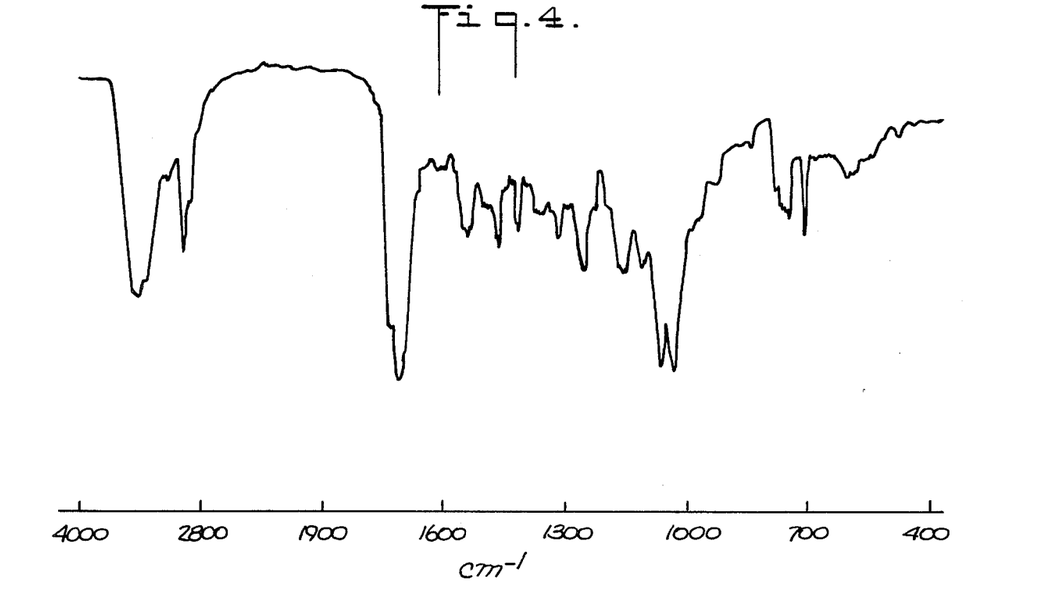

Analysis of purified 2'-N, 6'-N-dicarbobenzoxy XK-62-2 reveals the following:

Melting point : 93–95° C. Specific rotation: $[\alpha]_D^{18} = +81.6°$ (c=0.12, methanol) Infrared absorption spectrum (KBr) (cm$^{-1}$) [FIG. 4] : 3,800–3,000, 2,950, 1,700, 1,540, 1,456, 1,403, 1,310, 1,250, 1,160, 1,050, 1,010, 960, 738, 700, 605. Nuclear magnetic resonance spectrum (in methanol -d$_4$) δ (in p.p.m. from TMS) [FIG. 1] : 1.13 (3H, singlet), 2.62 (3H, singlet), 3.01 (3H, singlet), 5.30–4.90 (6H, broad, singlet), 7.43 (5H, singlet), 7.47 (5H, singlet)

Elementary analysis: Calculated for $C_{36}H_{55}N_5O_{12}\cdot\frac{1}{2}H_2O$: C=58.10%; H=7.29%; N=9.46%. Found: C=58.02%; H=7.51%; N=9.70%.

EXAMPLE 3

Production of 6'-N-carbobenzoxy XK-62-2

In this example, the water layer obtained after extraction with ethyl acetate in Example 2 is concentrated to about 15 ml under reduced pressure. The resulting concentrate is charged into a column having a diameter of 2.5 cm packed with 200 ml of an ion exchange resin, Amberlite CG-50 (ammonium form) (Product of Rohm and Haas Co., U.S.A.). The column is washed with 200 ml of water. Elution is then carried out with 0.1N aqueous ammonia and the eluate is taken in 10 ml portions. 6'-N-carbobenzoxy XK-62-2 is eluted out in fraction Nos. 48–65. These fractions are combined and concentrated to dryness under reduced pressure. As the result, 1.23 g of a colorless, amorphous solid is obtained. Yield: 23.1%. The thus obtained sample may be directly used as a starting material for the subsequent reaction. However, if desired, the product may be further purified by the above-described ion exchange resin treatment.

Figure 5:
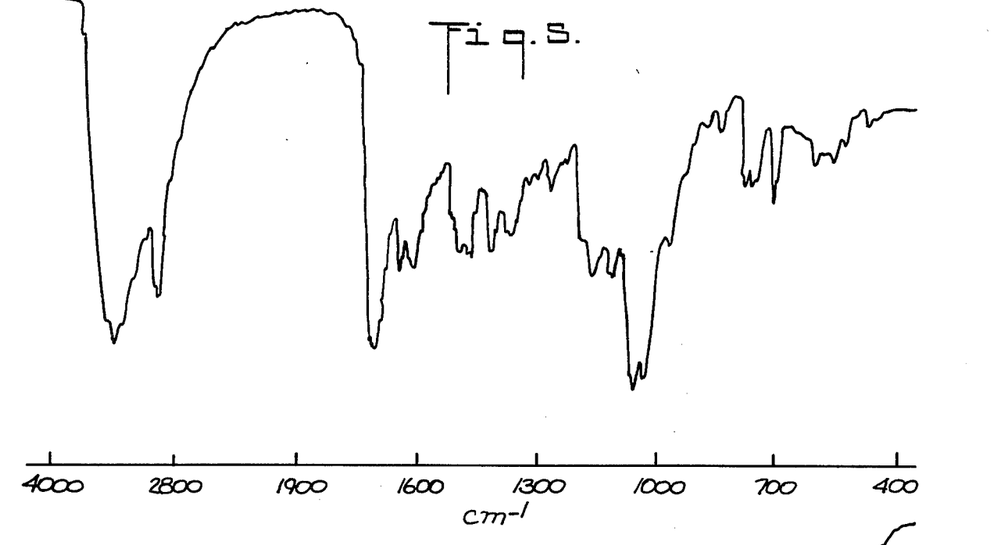

Analysis of the purified 6'-N-carbobenzoxy XK-62-2 reveals the following:

Melting point: 108–110° C. Specific rotation: $[\alpha]_D^{18} = +127.8°$ (c=0.094, methanol) Infrared absorption spectrum (KBr, cm$^{-1}$) [FIG. 5] : 3,700–3,000, 2,930, 1,690, 1,630, 1,596, 1,480, 1,452, 1,402, 1,250, 1,143, 1,096, 1,050, 1,020, 830, 768, 750, 697, 595, 550

Figure 2:
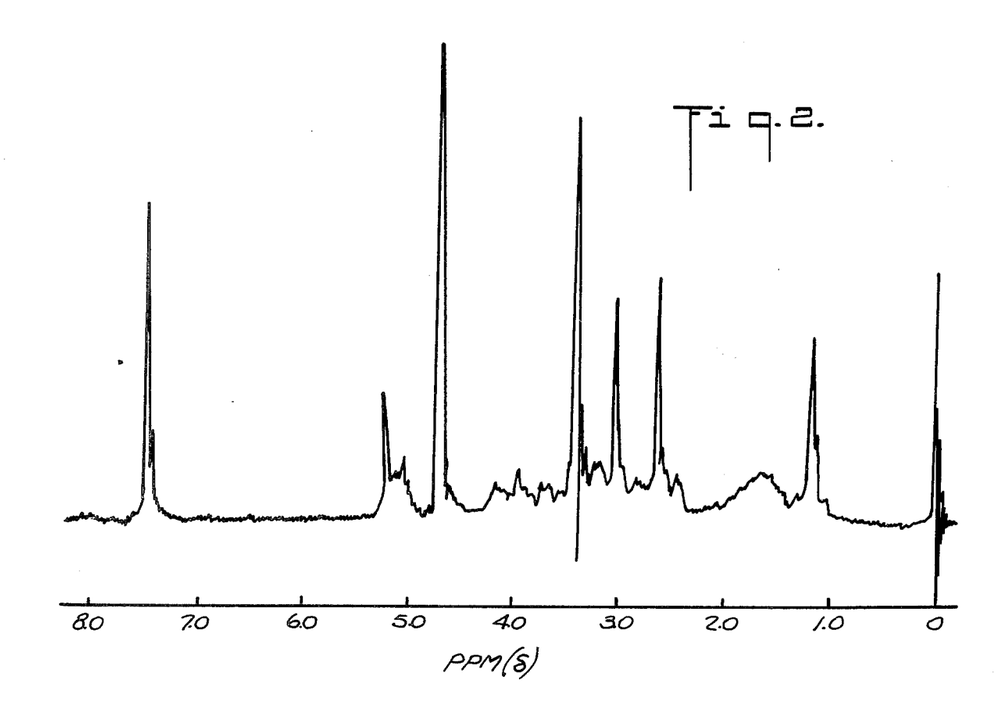

Nuclear magnetic resonance spectrum (in methanol —d$_4$) δ (in p.p.m. from TMS) [FIG. 2] : 1.16 (3H, singlet), 2.61 (3H, singlet), 3.01 (3H, singlet), 5.30–4.90 (4H, multiplet), 7.47 (5H, singlet)

Elementary analysis: Calculated for $C_{28}H_{47}N_5O_9\cdot H_2O$: C=54.77%; H=7.84%; N=11.13%. Found: C=54.91%; H=7.93%; N=10.90%.

EXAMPLE 4

Production of 2'-N-carbobenzoxy XK-62-2

In this example, following the elution of 6'-N-carbobenzoxy XK-62-2 in Example 3, 2'-N-carbobenzoxy XK-62-2 is eluted out in fractions Nos. 78–97. These fractions are combined and concentrated to dryness under reduced pressure to obtain 1.43 g of 2'-N-carbobenzoxy XK-62-2 as a colorless, amorphous solid. Yield: 26.7%. The thus obtained sample may be directly used as a starting material for the subsequent reaction. However, if desired, the product may be further purified by treatment with an ion exchange resin in the same manner as in Example 3.

Analysis of the purified 2'-N-carbobenzoxy XK-62-2 reveals the following:

Melting point: 107–110° C. Specific rotation: $[\alpha]_D^{25} = +87.80°$ (C=0.10, water)

Figure 6:
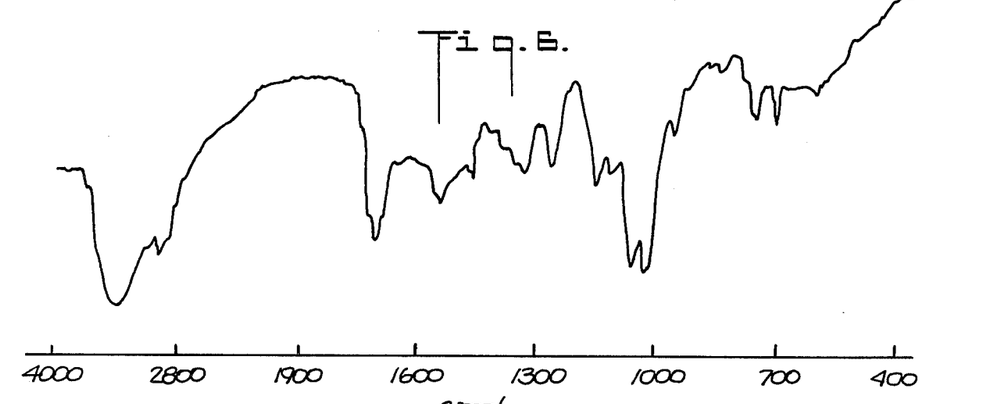

Infrared absorption spectrum (KBr) (cm$^{-1}$) [FIG. 6] : 3,700–3,100, 2,930, 1,702, 1,530, 1,451, 1,310, 1,255, 1,141, 1,053, 1,021, 960, 735, 697, 604

Figure 3:
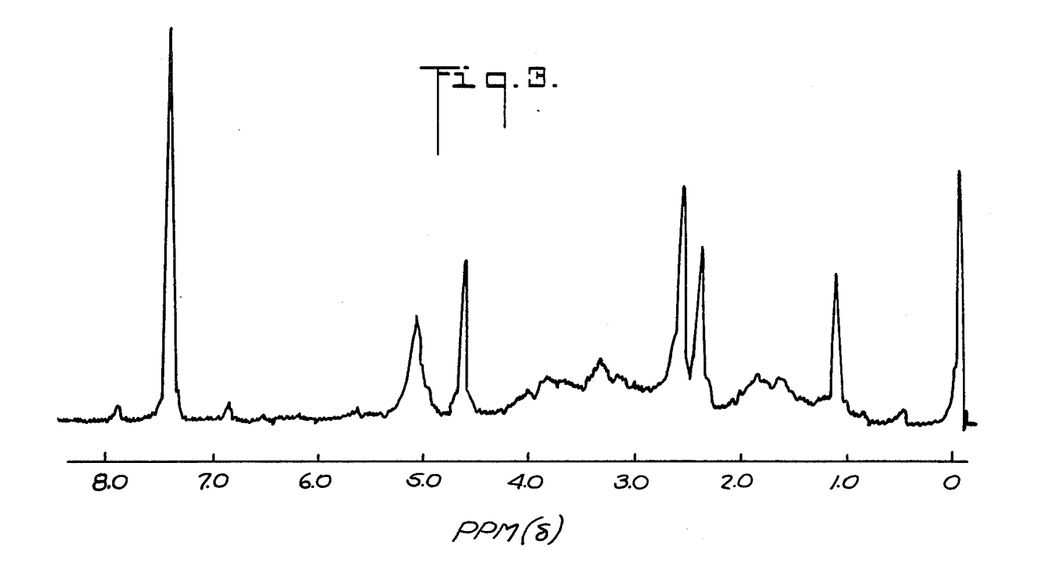

Nuclear magnetic resonance spectrum (in methanol -d$_4$) δ (in p.p.m. from TMS) [FIG. 3] : 1.13 (3H, singlet), 2.42 (3H, singlet), 2.60 (3H, singlet), 5.13 (4H, broad, singlet) 7.43 (5H, singlet)

Elementary analysis: Calculated for $C_{28}H_{47}N_5O_9\cdot 2H_2O$: C=53.08%; H=8.06%; N=11.06%. Found: C=53.31%; H=8.16%; N=10.93%.

EXAMPLE 5

Production of N-hydroxysuccinimide ester of α-hydroxy-β-carbobenzoxyaminopropionic acid In this example, 1.0 g (4.2 mmoles) of α-hydroxy-β-carbobenzoxyaminopropionic acid [The compound is described in The Carbohydrate Research, Vol. 28, pages 263–280 (1973)] and 0.48 g (4.2 mmoles) of N-hydroxysuccinimide are dissolved in 35 ml of ethylacetate. To the solution is added 0.86 g (4.2 mmoles) of dicyclohexylcarbodiimide with stirring while maintaining the temperature at 0° C. to 5° C. The mixture is allowed to stand at the same temperature overnight. The separated dicyclohexylurea is removed by filtration. The resulting filtrate is concentrated under reduced pressure to remove ethylacetate. As the result, 1.30 g of N-hydroxysuccinimide ester of α-hydroxy-β-carbobenzoxyaminopropionic acid is obtained as a colorless, transparent oily matter. Yield : 92.0%. The thus obtained product may be used as is for the subsequent reaction. However, if necessary, the product may be further purified by column chromatography and other well-known methods.

Analysis of the purified product reveals the following:

Infrared absorption spectrum (liquid film, cm$^{-1}$) : 3,700–3,100, 2,950, 1,816, 1,780, 1,700, 1,520, 1,320, 1,170, 1,070, 992, 830–500

Nuclear magnetic resonance spectrum (in deuteriochloroform) δ (in p.p.m. from TMS) : 2.77 (4H, singlet), 3.67 (2H, multiplet), 4.64 (1H, multiplet), 5.11 (2H, singlet), 5.82 (1H, triplet J=3.0 Hz), 7.33 (5H, singlet)

Elementary analysis: Calculated for $C_{15}H_{16}N_2O_7$: C=53.57%; H=4.76%; N=8.33%. Found: C=53.42; H=4.65%; N=8.39%.

EXAMPLE 6

Production of 1-N-(α-hydroxy-β-carbobenzoxyamino-propionyl)-2'-N, 6'-N-dicarbobenzoxy XK-62-2

In this example, 740 mg (1.0 mmole) of 2'-N, 6'-N-dicarbobenzoxy XK-62-2 is dissolved in 20 ml of aqueous 50% dimethylformamide. To the solution is added dropwise a solution of 403 mg (1.2 mmole) of N-hydroxysuccinimide ester of α-hydroxy-β-carbobenzoxyaminopropionic acid in 15 ml of dimethylformamide with stirring while maintaining the temperature at −5° C. to 0° C. The addition is complete in one hour. The mixture is then allowed to react overnight. By silica gel thin layer chromatography (under the same conditions as in Example 1), the presence of a small amount of by-products and unreacted 2'-N, 6'-N-dicarbobenzoxy XK-62-2 in addition to 1-N-(α-hydroxy-β-carbobenzoxyaminopropionyl)-2'-N, 6'-N-dicarbobenzoxy XK-62-2 (Rf : 0.95) is detected. The reaction mixture is concentrated under reduced pressure to obtain a slightly yellowish residue. The residue is used for the subsequent reaction without purification. If desired, the product may be purified by silica gel column chromatography in the same manner as in Example 1.

EXAMPLE 7

Production of 1-N-(α-hydroxy-β-carbobenzoxyaminopropionyl)-2'-N-carbobenzoxy XK-62-2

In this example, 633 mg (1.0 mmole) of 2'-N-carbobenzoxy XK-62-2 is dissolved in 20 ml of aqueous 50% dimethylformamide. To the solution is added dropwise a solution of 403 mg (1.2 mmole) of N-hydroxysuccinimide ester of α-hydroxy-β-carbobenzoxyaminopropionic acid in 15 ml of dimethylformamide with stirring while maintaining the temperature at −5° C. to 0° C. The addition is complete in one hour. The mixture is then allowed to react overnight. By silica gel thin layer chromatography (under the same conditions as in Example 1), the presence of a small amount of by-products and unreacted 2'-N-carbobenzoxy XK-62-2 in addition to 1-N-(α-hydroxy-β-carbobenzoxyaminopropionyl)-2'-N-carbobenzoxy XK-62-2 (Rf : 0.83) is detected. The reaction mixture is concentrated under reduced pressure to obtain a slightly yellowish residue. The residue is used for the subsequent reaction without purification. If desired, the product may be purified by silica gel column chromatography in the same manner as in Example 1.

EXAMPLE 8

Production of 1-N-(α-hydroxy-β-carbobenzoxyaminopropionyl)-6'-N-carbobenzoxy XK-62-2

In this example 615 mg (1.0 mmole) of 6'-N-carbobenzoxy XK-62-2 is dissolved in 20 ml of aqueous 50% dimethylformamide. To the solution is added dropwise a solution of 403 mg (1.2 mmole) of N-hydroxysuccinimide ester of α-hydroxy-β-carbobenzoxyaminopropionic acid in 15 ml of dimethylformamide with stirring while maintaining the temperature at −5° C. to 0° C. The addition is complete in one hour. The mixture is then allowed to react overnight. By silica gel thin layer chromatography (under the same conditions as in Example 1), the presence of a small amount of by-products and unreacted 6'-N-carbobenzoxy XK-62-2 in addition to 1-N-(α-hydroxy-β-carbobenzoxyaminopropionyl)-6'-N-carbobenzoxy XK-62-2 (Rf : 0.87) is detected. The reaction mixture is concentrated under reduced pressure to obtain a slightly yellowish residue. The residue is used for the subsequent reaction without purification. If desired, the product may be purified by ion exchange resin treatment in the same manner as in Example 3.

EXAMPLE 9

Production of 1-N-(α-hydroxy-β-aminopropionyl) XK-62-2

In this example, the residue obtained in Example 6 containing 1-N-(α-hydroxy-β-carbobenzoxyaminopropionyl)-2'-N, 6'-N-dicarbobenzoxy XK-62-2 as a main component is dissolved in 20 ml of aqueous 20% methanol. To the solution is added 1.0 ml of acetic acid and the mixture is subjected to hydrogenolysis in the presence of 120 mg of 5% active carbon-palladium catalyst at room temperature and atmospheric pressure for 6 hours. By silica gel thin layer chromatography (developer : isopropanol : concentrated aqueous ammonia : chloroform = 2 : 1 : 1, color reagent : ninhydrin), the presence of 1-N-(α-hydroxy-β-aminopropionyl) XK-62-2 (Rf : 0.42) as a main component, its positional isomers and a small amount of XK-62-2 (due to unreacted 2'-N, 6'-N-dicarbobenzoxy XK-62-2 in Example 6) is confirmed. The catalyst is removed by filtration and the filtrate is concentrated under reduced pressure. The residue is then dissolved in 10 ml of water and the solution is charged into a column (diameter : 1.5 cm) of 70 ml of ion exchange resin, Amberlite CG-50 (ammonium form). The column is washed with 200 ml of water and then 0.2N aqueous ammonia is passed through the column to recover XK-62-2 (58 mg). Elution is carried out with 0.4N aqueous ammonia while checking the components by thin layer chromatography. The fractions containing 1-N-(α-hydroxy-β-aminopropionyl) XK-62-2 (Rf : 0.42) as the only component are combined and evaporated to dryness under reduced pressure to obtain 371 mg of a colorless, amorphous solid. Yield : 58.1% from 2'-N, 6'-N-dicarbobenzoxy XK-62-2.

Figure 7:
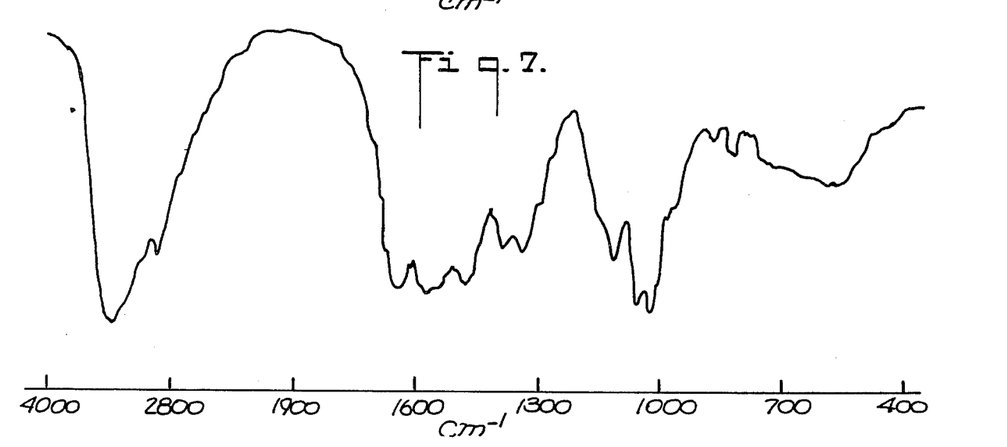

Analysis of the product reveals the following:

Melting point: 149–152° C. (decomposed at 160° C.)
Specific rotation: $[\alpha]_D^{18} = +91.5°$ (c=0.106, water)
Infrared absorption spectrum (KBr, cm$^{-1}$) [FIG. 7] : 3,800–3,000, 2,930, 1,650, 1,570, 1,480, 1,385, 1,330, 1,110, 1,052, 1,020, 813

Elementary analysis:
Calculated for $C_{23}H_{46}N_6O_9 \cdot H_2CO_3 \cdot 1.5H_2O$: C=45.07% H=7.98%; N=13.14%. Found: C=45.21%; H=7.71%; N=13.32%.

EXAMPLE 10

Production of 1-N-(α-hydroxy-β-aminopropionyl) XK-62-2

In this example, the residue obtained in Example 7 containing 1-N-(α-hydroxy-β-carbobenzoxyaminopropionyl)-2'-N-carbobenzoxy XK-62-2 as a main component is dissolved in 20 ml of aqueous 20% methanol. To the solution is added 1.0 ml of acetic acid and the mixture is subjected to hydrogenolysis in the presence of 110 mg of 5% active carbon-palladium catalyst at room temperature and atmospheric pressure for 6 hours. After the completion of reaction, the reaction mixture is treated in the same manner as described in Example 9 to obtain 397 mg of 1-N-(α-hydroxy-β-aminopropionyl) XK-62-2. Yield : 62.1% from 2'-N-carbobenzoxy XK-62-2.

EXAMPLE 11

Production of 1-N-(α-hydroxy-β-aminopropionyl) XK-62-2

In this example, the residue obtained in Example 8 containing 1-N-(α-hydroxy-β-carbobenzoxyaminopropionyl)-6'-N-carbobenzoxy XK-62-2 as a main component is dissolved in 20 ml of aqueous 20% methanol. To the solution is added 1.0 ml of acetic acid and the mixture is subjected to hydrogenolysis in the presence of 110 mg of 5% active carbonpalladium catalyst at room temperature and atmospheric pressure for 6 hours. After the completion of reaction, the reaction mixture is treated in the same manner as described in Example 9 to obtain 243 mg of 1-N-(α-hydroxy-β-aminopropionyl) XK-62-2. Yield : 38.1% from 6'-N-carbobenzoxy XK-62-2.

EXAMPLE 12

Production of 1-N-(α-hydroxy-β-aminopropionyl) XK-62-2 monosulfate

In this example, 6.39 g (10 mmoles) of 1-N-(α-hydroxy-β-aminopropionyl) XK-62-2 is dissolved in 20 ml of water. To the solution is added a solution of 0.98 g (10 mmoles) of sulfuric acid in 5.0 ml of water under cooling. After 30 minutes, cold ethanol is added to the solution until precipitation is complete. The white precipitate is separated by filtration to obtain the monosulfate of 1-N-(α-hydroxy-β-aminopropionyl) XK-62-2.

EXAMPLE 13

Production of 1-N-(α-hydroxy-β-carbobenzoxyaminopropionyl) XK-62-2

In this example, 2.79 g (6.0 mmoles) of XK-62-2 is dissolved in 50 ml of aqueous 50% dimethylformamide. To the solution is added dropwise a solution of 2.82 g (8.4 mmoles) of N-hydroxysuccinimide ester of α-hydroxy-β-carbobenzoxyaminopropionic acid in 20 ml of dimethylformamide with stirring while maintaining the temperature at −5° C. to 0° C. The addition is complete in one hour. The mixture is allowed to react overnight. By silica gel thin layer chromatography (developer:isopropanol : concentrated aqueous ammonia : chloroform = 4 : 1 : 1, color reagent : ninhydrin), the presence of 1-N-(α-hydroxy-β-carbobenzoxyaminopropionyl) XK-62-2 (Rf : 0.63), by-products and unreacted XK-62-2 is detected. The reaction mixture is concentrated under reduced pressure to obtain a slightly yellowish residue containing 1-N-(α-hydroxy-β-carbobenzoxyaminopropionyl) XK-62-2. The residue is used for the subsequent reaction without purification.

EXAMPLE 14

Production of 1-N-(α-hydroxy-β-aminopropionyl) XK-62-2

In this example, the residue obtained in Example 13 is dissolved in 40 ml of aqueous 50% methanol. To the solution is added 0.6 ml of acetic acid and the mixture is subject to hydrogenolysis in the presence of 250 mg of 5% active carbon-palladium catalyst at room temperature and at atmospheric pressure for 6 hours. By silica gel thin layer chromatography (developer : isopropanol : concentrated aqueous ammonia : chloroform = 2 : 1 : 1) the presence of 1-N-(α-hydroxy-β-aminopropionyl) XK-62-2, its positional isomers and a small amount of XK-62-2 is confirmed. The catalyst is removed by filtration and the filtrate is concentrated under reduced pressure. To the residue is added 15 ml of water and the solution is charged into a column (diameter :2.5 cm) containing 150 ml of an ion exchange resin, Amberlite CG-50 (ammonium form). The column is washed with 200 ml of water and then 0.2N aqueous ammonia is passed through the column to recover XK-62-2 (116 mg). Elution is carried out with 0.4N aqueous ammonia while checking the components by thin layer chromatography. The fractions containing 1-N-(α-hydroxy-β-aminopropionyl) XK-62-2 (Rf : 0.42) as the only component are combined and evaporated to dryness under reduced pressure to obtain 586 mg of a colorless, amorphous solid. Yield : 15.3%.

Analysis of the product reveals the following:
Melting point: 149–152° C (decomposed at 160° C.)
Specific rotation: $[\alpha]_D^{18} = +91.5°$ (c=0.106, water)
Infrared absorption spectrum (KBr, cm$^{-1}$) : 3,800–3,000, 2,930, 1,650, 1,570, 1,480, 1,385, 1,330, 1,110, 1,052, 1,020, 813
Elementary analysis:
Calculated for $C_{23}H_{46}N_6O_9 \cdot H_2CO_3 \cdot 1.5H_2O$: C=45.07%; H=7.98%; N=13.14%
Found: C=45.31%; H=7.54%, N=13.13%.

EXAMPLE 15

Production of 1-N-(α-hydroxy-β-aminopropionyl) XK-62-2

In this example, 926 mg (2.0 mmols) of XK-62-2 is dissolved in 100 ml of aqueous 50% dimethylformamide To the solution is added dropwise a solution of 1.18 g (5.4 m moles of N-ethoxycarbonylphthalimide in 10 ml of dimethylformamide with stirring while maintaining the temperature at 20° to 25° C. The addition is complete in 15 minutes. The mixture is allowed to react overnight. The reaction mixture contains 2'-N-phthaloyl XK-62-2 as a main component and is used for the subsequent reaction without isolation and purification.

To the reaction mixture is added dropwise a solution of 1.05 g (3.2 mmols) of N-hydroxysuccinimide ester of α-hydroxy-β-N-phthaloylpropionic acid in 10 ml of dimethylformamide while maintaining the temperature at 20° to 25° C. The addition is complete in 15 minutes. The mixture is allowed to react overnight. As a result, the reaction mixture containing 2'-N-phthaloyl-1-N-(α-hydroxy-β-N-phthaloylpropionyl) XK-62-2 as a main component is obtained.

To the reaction mixture is then added dropwise a solution of 12.9 g of aqueous 80% hydrazine in 70 ml of methanol while maintaining the temperature at 10° to 15° C. The addition is complete in 30 minutes. The mixture is allowed to react overnight to eliminate the phthaloyl group. The reaction mixture is concentrated under reduced pressure and the resulting residue is dissolved in 20 ml of water. By column chromatography using Amberlite CG-50 (ammonium form) under the same conditions as in Example 14, 685.5 mg of the desired 1-N-(α-hydroxy-β-aminopropionyl) XK-62-2 is obtained. Yield: 53.7%.

What is claimed is:

1. A compound having the formula:

or a non-toxic pharmaceutically acceptable acid addition salt thereof.